(12) United States Patent
Hirota et al.

(10) Patent No.: US 6,365,378 B1
(45) Date of Patent: Apr. 2, 2002

(54) METHOD FOR PRODUCING DNA CHIP

(75) Inventors: Toshikazu Hirota, Owariasahi; Motoo Noritake, Ichinomiya, both of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/694,157

(22) Filed: Oct. 23, 2000

(30) Foreign Application Priority Data

Oct. 22, 1999 (JP) .......................... 11-301627
Mar. 28, 2000 (JP) .......................... 12-089979

(51) Int. Cl.⁷ .................. C12P 19/34; C12M 1/00; C12Q 1/68; G01N 15/06; G01N 33/00; G01N 33/48; B01L 3/02
(52) U.S. Cl. .................. 435/91.1; 435/283.1; 435/6; 422/100; 422/68.1
(58) Field of Search .................. 422/100, 68.1; 435/6, 91.1

(56) References Cited

U.S. PATENT DOCUMENTS 6,024,925 A * 2/2000 Little et al. .................. 422/100
6,110,426 A * 8/2000 Shalon et al. .................. 422/68.1

FOREIGN PATENT DOCUMENTS

JP 6-040030 A 2/1994
JP 8-201265 A 8/1996

* cited by examiner

Primary Examiner—Kenneth R. Horlick
Assistant Examiner—Teresa Strzelecka
(74) Attorney, Agent, or Firm—Burr & Brown

(57) ABSTRACT

A PCR product is prepared by PCR-amplifying a DNA fragment. The PCR product is then dried to prepare a DNA powder. The DNA powder is then charged into a sample-pouring port of each of the micropipettes of a dispenser. Subsequently, a buffer solution is poured from the sample-pouring port into a cavity to prepare a sample solution. After completion of the preparation of the sample solution in the cavity, an actuator section is driven to discharge and supply the sample solution onto a base plate.

16 Claims, 9 Drawing Sheets

METHOD FOR PRODUCING DNA CHIP

BACKGROUND OF THE INVENTION

1. Field of the Invention

The present invention relates to a method for producing a DNA chip (DNA microarray) in which several thousand to not less than ten thousand different types of DNA fragments are aligned and fixed as minute spots at a high density on a base plate such as a glass microscope slide.

2. Description of the Related Art

Methods for analyzing genetic structure have been remarkably progressed in recent years. A large number of genetic structures represented by those of human genes have been clarified. The analysis of genetic structures as described above uses a DNA chip (DNA microarray) in which several thousand to not less than ten thousand different types of DNA fragments are aligned and fixed as minute spots on a base plate such as a glass microscope slide.

In general, the DNA chip is produced by arranging a plurality of minute spots of a sample solution containing DNA fragments on a base plate such as glass. Those widely used as a method for forming the minute spots are based on a system such as the QUILL system, the pin & ring system, and the solid pin system in which a sample solution containing DNA fragments is supplied (stamped) onto the base plate by using a so-called pin. Even when any one of the foregoing methods is adopted, it is necessary to suppress the dispersion of the volume and the shape of each of the minute spots to be low so that the distance between the respective minute spots is maintained to be constant.

The PCR amplification step is used to prepare the sample solution containing the DNA fragments. The sample solution is often used while performing the amplification up to an amount of liquid required for the spot starting from a slight amount of original DNA. The amount of liquid obtained by the amplification is about several tens of microliters, and the reagents required for the amplification are expensive. Therefore, it is desirable to conserve reagents, which yields a more efficient use of the obtained liquid.

On the other hand, it is also desirable to realize a higher spot density. In this regard, it is necessary to develop a new method in which the shape control performance is satisfactory for the minute spot, and excellent productivity is realized as well.

When the minute spots are formed on the base plate by supplying the sample solution, the sample solution is prepared by PCR-amplifying a DNA fragment in a preparation vessel such as a cartridge beforehand to prepare a PCR product, drying the obtained PCR product to give DNA powder, and dissolving the obtained DNA powder in a buffer solution.

The sample solution is charged in a supply apparatus. The sample solution is supplied onto the base plate by using the supply apparatus to form the minute spots on the base plate.

In this procedure, the step of preparing the sample solution and the step of supplying the sample solution are separate from each other. Therefore, it is necessary to additionally perform management between the steps, and it is required to provide an equipment for preserving the sample solution. Further, the sample solution more probably contacts with the atmospheric air, and hence it is feared that the quality of the sample solution is deteriorated.

Further, the following problem arises because the sample solution is prepared in the preparation vessel such as the cartridge. That is, when the sample solution after the preparation is transferred to a pipette, a part of the sample solution remains in the cartridge. Further, when the sample solution is supplied to the supply apparatus by the aid of a pipette, a part of the sample solution also remains in the pipette. This procedure is also disadvantageous in the efficiency of utilization of the sample solution.

SUMMARY OF THE INVENTION

The present invention has been made taking the foregoing problems into consideration, an object of which is to provide a method for producing a DNA chip, which makes it possible to perform a series of steps of the preparation of a sample solution to the supply process without deteriorating the quality of the sample solution, improve the efficiency of utilization of the sample solution, realize the simplification of the preservation equipment for the sample solution, realize inexpensive cost, and improve the quality of the DNA chip.

According to the present invention, there is provided a method for producing a DNA chip by supplying a large number of sample solutions onto a base plate, comprising the steps of PCR-amplifying a DNA fragment to prepare a PCR product; drying the PCR product to prepare DNA powder; supplying the DNA powder into a solution supply apparatus; and supplying a buffer solution into the supply apparatus to prepare a sample solution; wherein the sample solution in the supply apparatus is supplied onto the base plate by using the supply apparatus to produce the DNA chip.

That is, in the present invention, the process for mixing the DNA powder and the buffer solution to prepare the sample solution, and the step of supplying the sample solution onto the base plate are performed in the identical supply apparatus. By doing so, the sample solution in the preparation vessel is moved in a powder state into the supply apparatus. Accordingly, it is possible to reduce any sample residue adhered, for example, to the vessel wall in the preparation vessel. Further, for example, it is unnecessary to use any pipette to move or transfer the sample. Thus, it is possible to avoid the occurrence of any residue of the sample remained and discarded in the pipette.

According to another aspect of the present invention, there is provided a method for producing a DNA chip, comprising the steps of PCR-amplifying a DNA fragment to prepare a PCR product; supplying the prepared PCR product into a solution supply apparatus; drying the PCR product in the supply apparatus to prepare DNA powder; and supplying a buffer solution into the supply apparatus to prepare a sample solution; wherein the sample solution in the supply apparatus is supplied onto the base plate by using the supply apparatus to produce the DNA chip.

That is, in the present invention, the process for drying the PCR product to prepare the DNA powder, and the process for mixing the DNA powder and the buffer solution to prepare the sample solution are performed in the identical supply apparatus.

Accordingly, it is possible to reduce the loss which would be otherwise caused, for example, by any scattering of the sample in the drying step. Thus, it is possible to improve the efficiency of utilization of the sample solution. Further, the series of operations, i.e., from the preparation of the DNA powder to the supply process, are performed in one supply apparatus. Therefore, the sample solution scarcely contacts with the atmospheric air. Thus, it is possible to avoid any deterioration of the quality of the sample solution.

According to still another aspect of the present invention, there is provided a method for producing a DNA chip, comprising the steps of PCR-amplifying a DNA fragment to prepare a PCR product in a solution supply apparatus; drying the PCR product in the supply apparatus to prepare DNA powder; and supplying a buffer solution into the supply apparatus to prepare a sample solution; wherein the sample solution in the supply apparatus is supplied onto the base plate by using the supply apparatus to produce the DNA chip.

That is, in the present invention, the series of steps ranging from the PCR amplification to the supply process are performed in the identical supply apparatus. Accordingly, the steps from the preparation of the sample solution to the supply process can be performed in accordance with the series of steps without deteriorating the quality of the sample solution. Further, it is possible to realize the simplification of the preservation equipment for the sample solution. It is possible to reduce the cost and improve the quality of the DNA chip.

It is unnecessary to perform any step of transferring the sample solution to another vessel. Therefore, it is possible to further improve the efficiency of utilization of the sample solution. Further, the steps ranging from the amplification of DNA to the supply process are performed on one supply apparatus. Therefore, the sample solution scarcely contacts with the atmospheric air, and thus it is possible to avoid any deterioration of the quality of the sample solution.

According to still another aspect of the present invention, there is provided a method for producing a DNA chip, comprising the step of PCR-amplifying a DNA fragment to prepare a PCR product in a solution supply apparatus; wherein the sample solution after preparation in the supply apparatus is supplied onto the base plate by using the supply apparatus to produce the DNA chip.

That is, the PCR product, which is obtained by the PCR amplification in the supply apparatus, is directly supplied onto the base plate.

By doing so, in addition to the respective functions and effects of the inventions described above, the step of preparing the sample solution in the vessel is simplified. It is possible to efficiently produce the DNA chip in a short period of time. It is also preferable to pour a reagent to neutralize the action of any component that inhibits the hybridization action on the DNA chip, that is included in any reagent used during the amplification, or exists in the solution containing the PCR product in the supply apparatus.

It is preferable that the sample solution is supplied in accordance with an ink-jet system. In this case, it is preferable that the supply apparatus is a dispenser comprising a plurality of arranged micropipettes each including a pouring port for pouring the sample solution from the outside, a cavity for pouring and charging the sample solution thereinto, and a discharge port for discharging the sample solution, formed on at least one or more substrates, the micropipette further including a piezoelectric/electrostrictive element disposed on at least one wall surface of the substrate which forms the cavity so that the sample solution is movable in the cavity, and mutually different types of the sample solutions being discharged from the discharge ports of the respective micropipettes.

Accordingly, the sample solution is prepared by performing the steps of pouring, for example, the DNA powder obtained by drying each of the different kinds of PCR products, each of the different kinds of PCR products, original DNA before the PCR amplification and the buffer solution to dissolve the DNA powder therein, or PCR amplification reagents (for example, primers, enzyme, PCR buffer solution, dNTP's, distilled water) from the pouring ports into the plurality of cavities, and optionally drying the PCR product at the pouring port portion to prepare the DNA powder. After that, the piezoelectric/electrostrictive element is driven, and thus the different types of the sample solutions in the plurality of cavities can be discharged from the discharge ports to produce the DNA chip.

As described above, the supply apparatus based on the ink-jet system, in which the volume of the portion for storing the sample in the supply apparatus is about several to several tens of microliters, is suitable, for example, for the preparation of the sample solution, the amplification, the purification, and the production in the supply apparatus. The foregoing function can be simultaneously possessed, in addition to the formation of the spots onto the base plate as the original function of the supply apparatus. It is possible to produce the DNA chip extremely efficiently. Further, as described later, when the supply apparatus itself is made of ceramics which has a good thermal conductivity, for example, as compared with glass and plastics, the supply apparatus is preferred for the PCR amplification in which the thermal cycle is performed.

It is also preferable that completion of preparation of the sample solution in each of the plurality of cavities is recognized by sensing a change of a fluid characteristic in the cavity. The piezoelectric/electrostrictive element, which is formed on at least one wall surface of the substrate for forming the cavity, functions as a sensor for sensing the physical characteristic of the liquid in the cavity. Accordingly, it is possible to accurately detect the completion of preparation.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Exemplary embodiments of the method for producing the DNA chip according to the present invention will be explained below with reference to FIGS. 1 to 9.

A dispenser 30 as shown in FIGS. 1A to 1C and 2 is used for the method for producing the DNA chip according to the embodiment of the present invention.

The dispenser 30 includes, for example, ten micropipettes 34 which are arranged in five rows and two columns on the upper surface of a fixation plate 32 having a rectangular configuration. A group of the micropipettes 34, which are aligned in the direction of the respective columns, are fixed on the fixation plate 32 by the aid of a fixing jig 36 respectively.

Figure 1A:
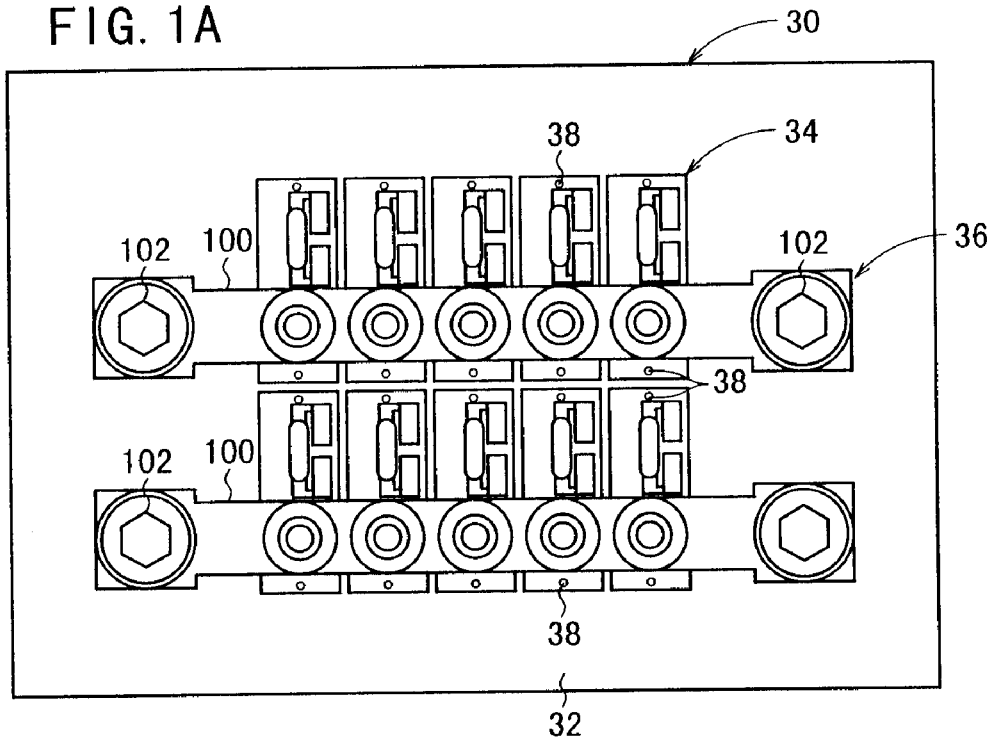
FIG. 1A shows a plan view illustrating an arrangement of a dispenser to be used for a method for producing a DNA chip according to an embodiment of the present invention.
Figure 1B:
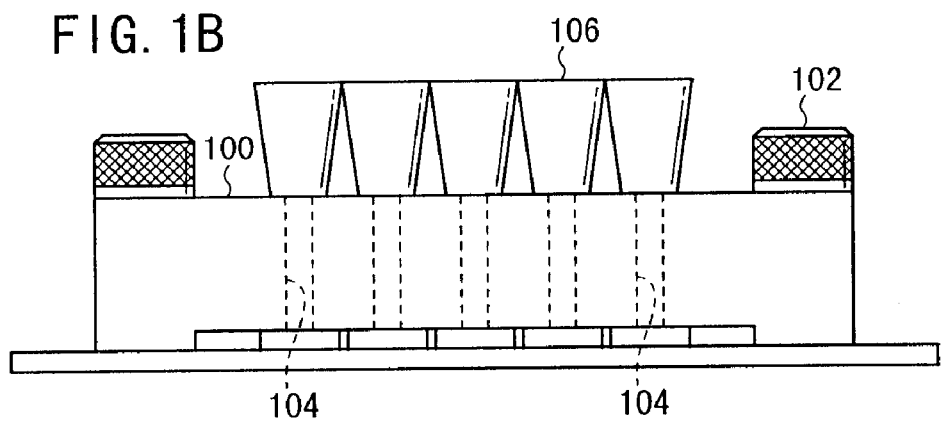
FIG. 1B shows a front view thereof.
Figure 1C:
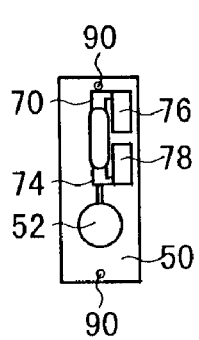
FIG. 1C shows a magnified plan view illustrating one micropipette for constructing the dispenser.
Figure 2:
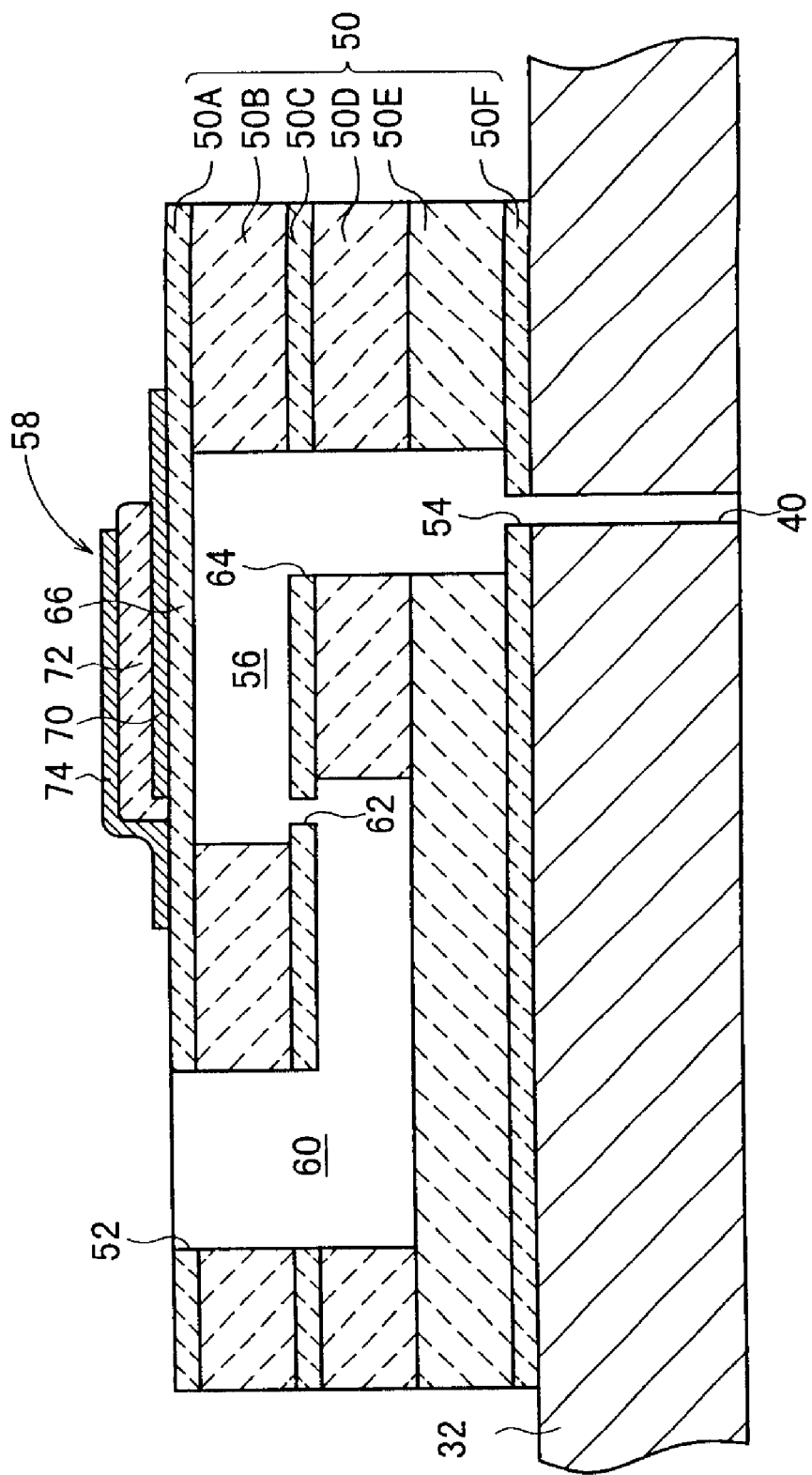
FIG. 2 shows a longitudinal sectional view illustrating an arrangement of the micropipette.
Figure 3:
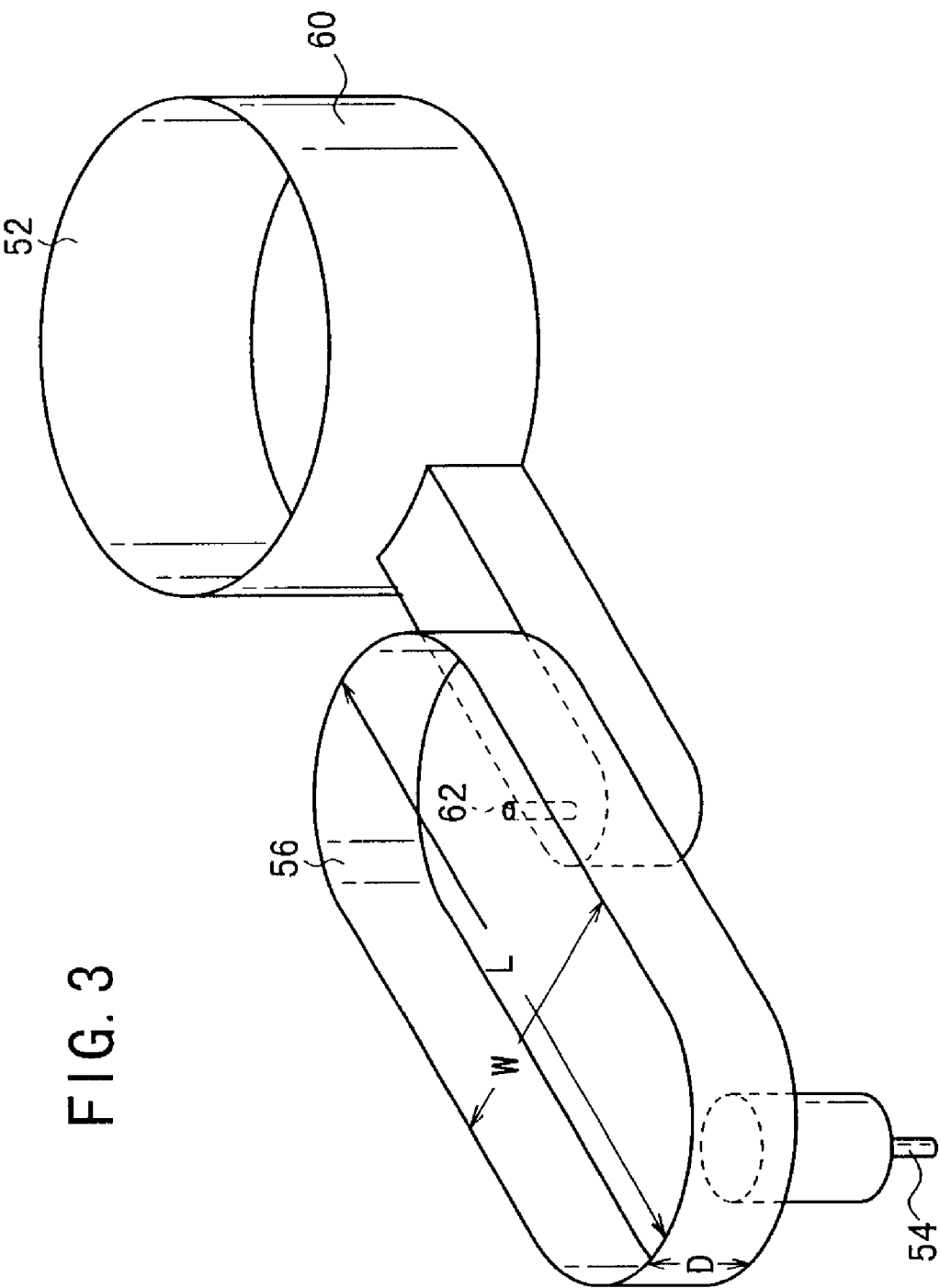
FIG. 3 shows a perspective view illustrating a shape of a flow passage including a cavity formed in a substrate of the micropipette.

As shown in FIGS. 1C and 2, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed at the inside between the sample-pouring port 52 and the sample discharge port 54, and an actuator section 58 which is used to vibrate the substrate 50 or change the volume of the cavity 56.

As shown in FIG. 2, through-holes 40 are provided through the fixation plate 32 at portions corresponding to the sample discharge ports 54 of the micropipettes 34 respectively. Accordingly, a sample solution, which is discharged from the sample discharge port 54 of the micropipette 34, is supplied through the through-hole 40, for example, to a base plate 10 (see FIG. 5) which is fixed under the fixation plate 32.

An introducing bore 60 having a substantially L-shaped configuration with a wide opening width is formed over a region ranging from the sample-pouring port 52 to the inside of the substrate 50 in the micropipette 34. A first communication hole 62 having a small diameter is formed between the introducing bore 60 and the cavity 56. The sample solution, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the embodiment of the present invention, the first communication hole 62 is formed at the lower surface of the cavity 56. The position of the first communication hole 62 is deviated toward the sample-pouring port 52. The second communication hole 64 is formed at a position of the lower surface of the cavity 56 as well as corresponding to the sample discharge port 54.

Further, in this embodiment, the portion of the substrate 50, with which the upper surface of the cavity 56 makes contact, is thin-walled to give a structure which tends to undergo a vibration with respect to external stress so that that portion functions as a vibrating section 66. The actuator section 58 is formed on the upper surface of the vibrating section 66.

The substrate 50 is constructed by laminating a plurality of green sheets made of zirconia ceramics (first thin plate layer 50A, first spacer layer 50B, second thin plate layer 50C, second spacer layer 50D, third spacer layer 50E, and third thin plate layer 50F), followed by sintering into one unit.

That is, the substrate 50 is constructed by laminating the thin-walled first thin plate layer 50A which is formed with a window for constructing the sample-pouring port 52 and which constitutes a part of the vibrating section 66, the thick-walled first spacer layer 50B which is formed with a part of the introducing bore 60 and a plurality of windows for constructing the cavity 56 respectively, the thin-walled second thin plate layer 50C which is formed with a part of the introducing bore 60 and a plurality of windows for constructing a part of the second communication hole 64 and the first communication hole 62 respectively, the thick-walled second spacer layer 50D which is formed with a plurality of windows for constructing a part of the introducing bore 60 and a part of the second communication hole 64 respectively, the thick-walled third spacer layer 50E which is formed with a window for constructing a part of the second communication hole 64, and the thin-walled third thin plate layer 50F which is formed with a window for constructing the sample discharge port 54, followed by sintering into one unit.

The actuator section 58 is constructed to have the vibrating section 66 described above as well as a lower electrode 70 which is directly formed on the vibrating section 66, a piezoelectric layer 72 which is composed of, for example, a piezoelectric/electrostrictive layer or an anti-ferroelectric layer formed on the lower electrode 70, and an upper electrode 74 which is formed on the upper surface of the piezoelectric layer 72.

As shown in FIG. 1C, the lower electrode 70 and the upper electrode 74 are electrically connected to an unillustrated driving circuit via a plurality of pads 76, 78 which are formed on the upper surface of the substrate 50 respectively.

The micropipette 34 constructed as described above is operated as follows. That is, when an electric field is generated between the upper electrode 74 and the lower electrode 70, the piezoelectric layer 72 is deformed, and the vibrating section 66 is deformed in accordance therewith. Accordingly, the volume of the cavity (pressurizing chamber) 56 contacting with the vibrating section 66 is decreased or increased.

Figure 5:
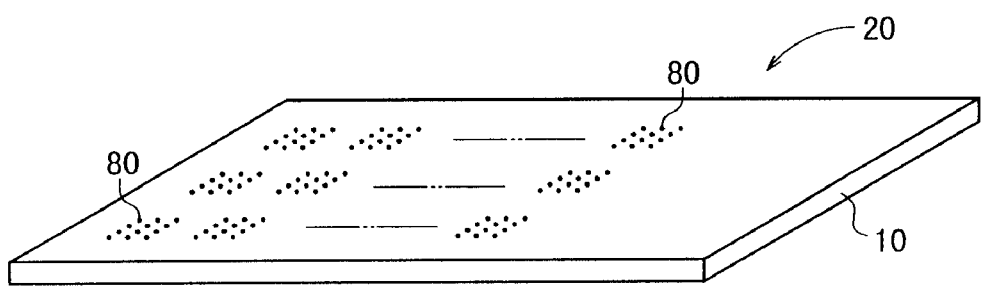
FIG. 5 shows a perspective view illustrating the DNA chip to be produced.

When the volume of the cavity 56 is decreased, the sample solution charged in the cavity 56 is discharged at a predetermined speed from the sample discharge port 54 which communicates with the cavity 56. As shown in FIG. 5, it is possible to produce a DNA chip 20 in which the sample solutions discharged from the micropipettes 34 are aligned and fixed as minute spots 80 on a base plate 10 such as a glass microscope slide. When the volume of the cavity 56 is increased, the sample solution is newly poured and charged from the first communication hole 62 into the cavity 56 to make provision for the next discharge.

An apparatus structure based on the so-called ink-jet system may be adopted as the structure in which the volume of the cavity 56 is decreased in accordance with the driving of the actuator section 58 (see Japanese Laid-Open Patent Publication No. 6-40030).

The cavity (pressurizing chamber) 56 is formed to have such a flow passage dimension that the sample solution containing DNA fragments or the like is moved without any turbulence.

That is, the dimension of the cavity 56 differs depending on the type of the sample, the size of liquid droplets to be prepared, and the density of spotting formation. However, for example, when DNA fragments ranging in length from about 1 to 10,000 base pairs are dissolved in a ×1 TE buffer solution at a concentration of not more than 100 $\mu$g/$\mu$l, and a sample, which is obtained by mixing with an aqueous solution containing an equivalent amount of polymer, is supplied at a pitch of 50 to 600 $\mu$m to give a liquid droplet diameter of 30 to 500 $\mu$m, then it is preferable that the cavity length (L) is 1 to 5 mm, the cavity width (W) is 0.1 to 1 mm, and the cavity depth (D) is 0.1 to 0.5 mm as shown in FIG.

3. It is preferable that the inner wall of the cavity 56 is smooth without involving any projection to disturb the flow. It is more preferable that the material of the cavity 56 is made of ceramics which has good affinity with respect to the sample solution.

When the shape as described above is adopted, the cavity 56 can be used as a part of the flow passage ranging from the sample-pouring port 52 to the sample discharge port 54. The sample can be introduced to the sample discharge port 54 without disturbing the flow of the sample solution which is moved from the sample-pouring port 52 via the introducing bore 60 and the first communication hole 62 to the inside of the cavity 56.

The substrate 50 is the sintered product obtained by laminating the zirconia ceramics into one unit as described above. Alternatively, the substrate 50 may be a bonded product composed of sintered zirconia ceramics formed with the actuator section 58, and a metal or resin film or the like. Especially, the thin plate layer 50F, in which the sample discharge port 54 is formed, is preferably a sheet obtained by processing an organic resin such as a PET film by means of an excimer laser or the like, or a sheet obtained by punching a metal such as a stainless steel film with a punch and die or the like, considering the matching with the processing method therefor.

The sizes of the sample discharge port 54 and the first communication hole 62 are optimally designed depending on, for example, the physical property, the discharge amount, and the discharge speed of the sample solution to be discharged. However, they are preferably about 10 to 100 µm.

As shown in FIG. 1A, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 1C) provided at both sides of the substrate 50 of the micropipette 34. Thus, a plurality of micropipettes 34 are automatically aligned and positioned with a predetermined array arrangement.

Each of the fixing jigs 36 has a holder plate 100 for pressing the plurality of micropipettes 34 against the fixation plate 32. Insertion holes for inserting screws 102 thereinto are formed through both end portions of the holder plate 100. When the screws 102 are inserted into the insertion holes, and they are screwed into the fixation plate 32, then the plurality of micropipettes 34 can be concurrently pressed against the fixation plate 32 by the aid of the holder plate 100. One unit is constructed by a plurality of micropipettes 34 which are pressed by one holder plate 100. The example shown in FIG. 1A is illustrative of the case in which one unit is constructed by five micropipettes 34 which are arranged in the direction of the column.

The holder plate 100 is formed with introducing holes 104 (see FIG. 1B) which are used to supply the sample solutions to the portions corresponding to the sample-pouring ports 52 of the respective micropipettes 34 respectively when the plurality of micropipettes 34 are pressed. Tubes 106 for introducing the sample solution to the introducing holes 104 respectively are held at the upper end portions of the respective introducing holes 104.

Considering the realization of an efficient wiring operation, it is preferable that the width of the holder plate 100 resides in such a dimension that the pads 76, 78 connected to the respective electrodes 70, 74 of the actuator section 58 are faced upwardly when the plurality of micropipettes 34 are pressed against the fixation plate 32.

As described above, the dispenser 30 is constructed such that the plurality of micropipettes 34 each having the sample-pouring port 52 and the sample discharge port 54 are provided in an upstanding manner with the respective sample discharge ports 54 directed downwardly.

That is, the respective micropipettes 34 are aligned and arranged such that the respective sample-pouring ports 52 are disposed on the upper side, the sample discharge ports 54 are disposed on the lower side, and the respective sample discharge ports 54 are aligned two-dimensionally. Sample solutions of mutually different types are discharged from the sample discharge ports 54 respectively.

Figure 4:
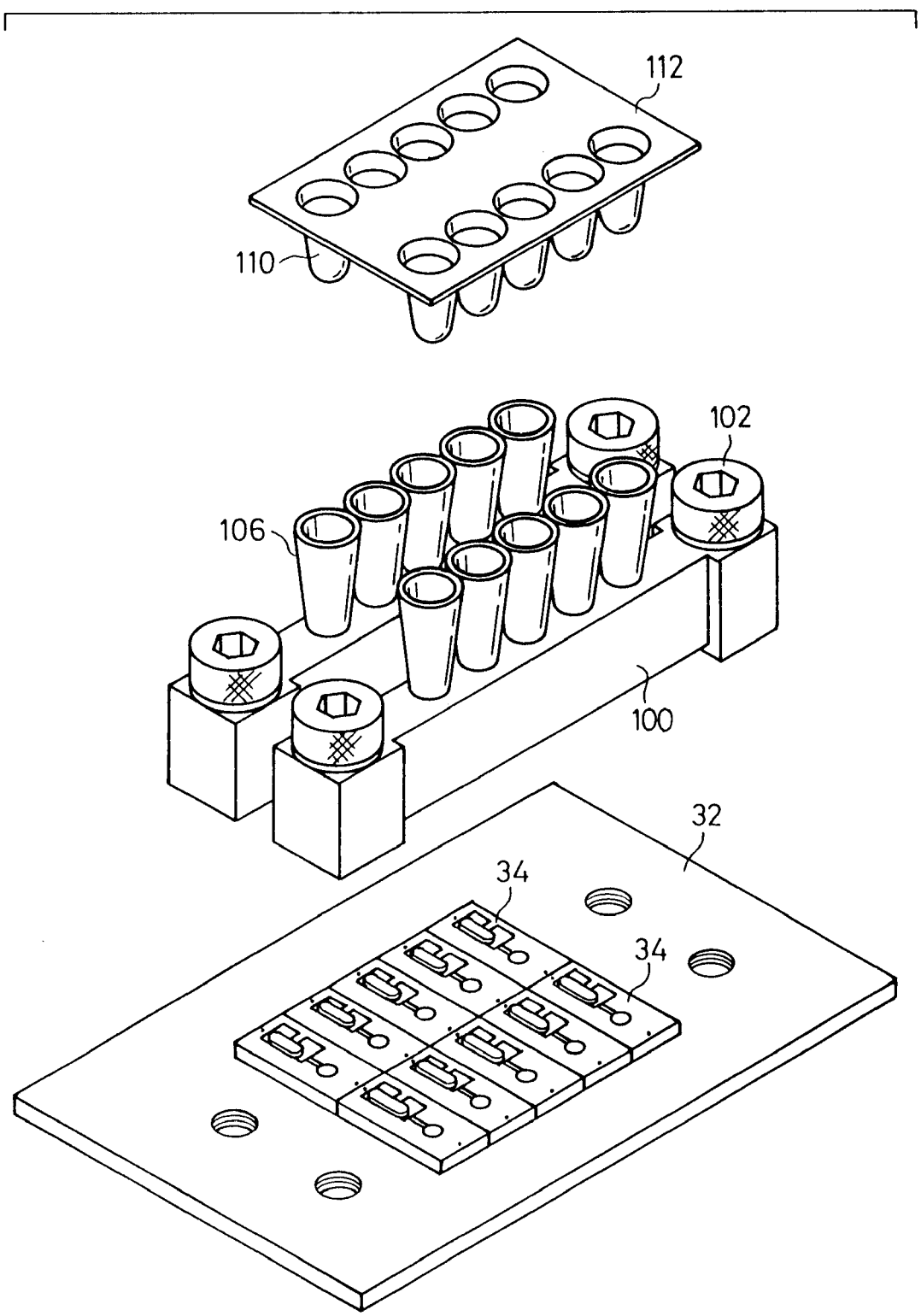
FIG. 4 shows an exploded perspective view illustrating the dispenser together with a cartridge.

When the dispenser 30 constructed as described above is used, several methods are available to supply the sample solutions of mutually different types corresponding to the respective sample-pouring ports 52. That is, as shown in FIG. 4, for example, a method is available, which is based on the use of a cartridge 112 arranged with a large number of recesses (storage sections) 110 each having a substantially V-shaped cross section. For this method, for example, the following procedure is available. That is, the mutually different sample solutions are poured into the respective recesses 110 of the cartridge 112. The cartridge 112 is attached so that the respective recesses 110 correspond to the tubes 106 respectively. The bottoms of the respective recesses 110 are opened with needles or the like. Accordingly, the sample solutions in the respective recesses 110 are supplied via the tubes 106 to the respective micropipettes 34.

When the tubes 106 are not used, for example, the following method is available. That is, the cartridge 112 is attached so that the respective recesses 110 correspond to the respective introducing holes 104 of the fixing jig 36. The bottoms of the respective recesses 110 are opened with needles or the like. Accordingly, the sample solutions in the respective recesses 110 are supplied via the introducing holes 104 to the respective micropipettes 34. Alternatively, needles or the like may be formed in the vicinity of the respective introducing holes 104 of the fixing jig 36 so that the respective recesses 110 may be opened simultaneously with the attachment of the cartridge 112 to the fixing jig 36.

Alternatively, it is also preferable to add a mechanism for feeding the gas or the like under pressure after the opening to forcibly extrude the sample solutions. It is desirable to provide a mechanism for washing the space ranging from the sample-pouring port 52 to the sample discharge port 54 formed at the inside of the substrate 50 of each of the micropipettes 34 so that several thousand different types of DNA fragments can be discharged as the minute spots 80 with good purity and without involving any contamination.

In the example shown in FIG. 1A, both ends of the holder plate 100 are tightened to the fixation plate 20 by the aid of screws 102. However, the holder plate 100 may be fixed in accordance with other methods based on the mechanical procedure by using screws and springs, as well as based on an adhesive or the like.

As described above, the substrate 50 for constructing the micropipette 34 is formed of ceramics, for which it is possible to use, for example, fully stabilized zirconia, partially stabilized zirconia, alumina, magnesia, and silicon nitride.

Among them, fully stabilized/partially stabilized zirconia is more preferable, because the mechanical strength is large even in the case of a thin plate, the toughness is high, and the reactivity with the piezoelectric layer 72 and the electrode material is small.

When fully stabilized/partially stabilized zirconia is used as the material, for example, for the substrate 50, it is preferable that the portion (vibrating section 66), on which the actuator section 58 is formed, contains an additive such as alumina and titania.

Those usable as the piezoelectric ceramic for the piezoelectric layer 72 for constructing the actuator section 58 include, for example, lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate, as well as composite ceramics containing components obtained by combining any of them. However, in the embodiment of the present invention, a material containing a major component composed of lead zirconate, lead titanate, and lead magnesium niobate is preferably used, because of the following reason.

That is, such a material has a high electromechanical coupling constant and a high piezoelectric constant. Additionally, such a material has small reactivity with the substrate material during the sintering of the piezoelectric layer 72, making it possible to stably form a product having a predetermined composition.

Further, in the embodiment of the present invention, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or other compounds.

For example, it is also preferable to use ceramics containing a major component composed of lead zirconate, lead titanate, and lead magnesium niobate, and further containing lanthanum and/or strontium.

On the other hand, it is preferable that the upper electrode 74 and the lower electrode 70 of the actuator section 58 are made of metal which is solid at room temperature and which is conductive. For example, it is possible to use aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or an alloy obtained by combining any of them. It is also preferable to use a cermet material obtained by dispersing, in the metal described above, the same material as that of the piezoelectric layer 72 or the substrate 50.

Next, an explanation will be made with reference to FIGS. 6 to 9 for the method for producing the DNA chip according to the embodiment of the present invention based on the use of the dispenser 30.

Figure 6:
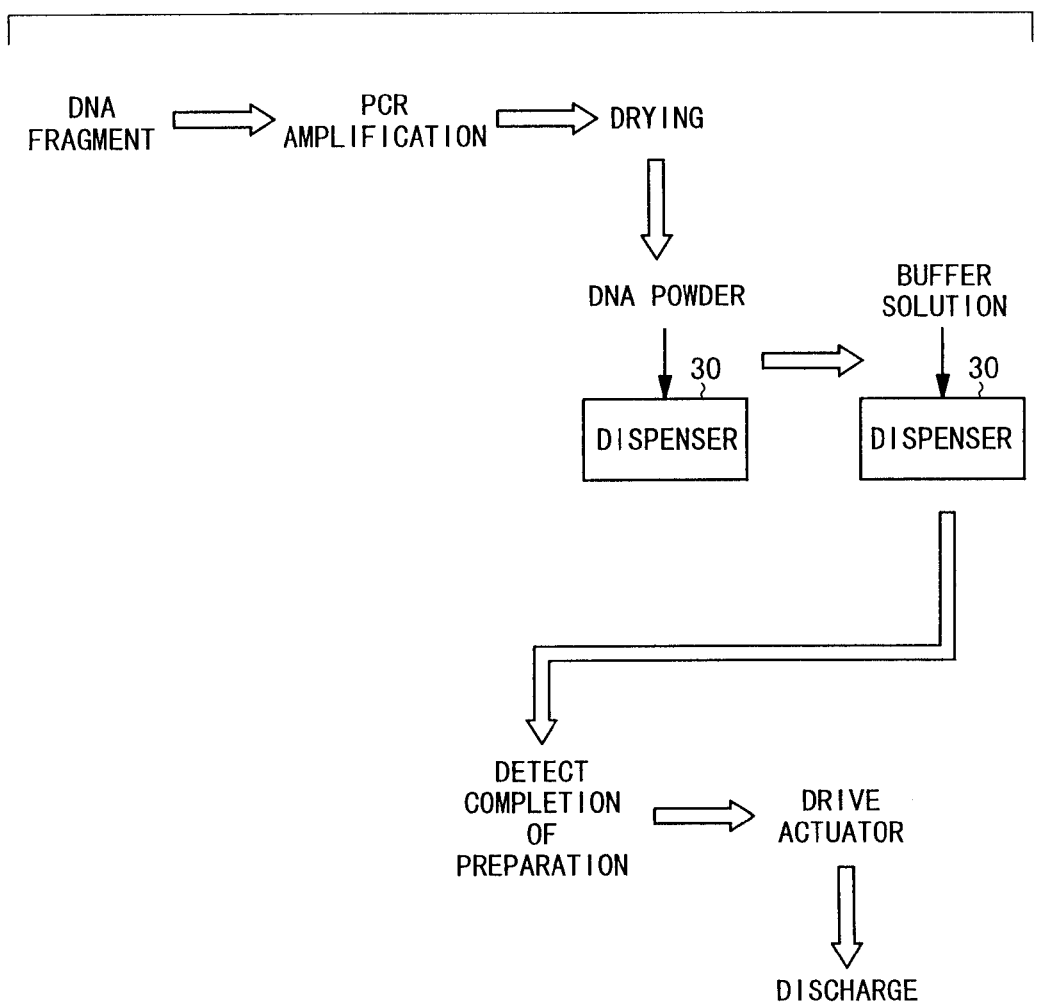
FIG. 6 illustrates a production method according to a first embodiment.

At first, a production method according to a first embodiment is shown in FIG. 6. A DNA fragment is amplified to prepare a PCR product. After that, the PCR product is dried to prepare DNA powder. After that, the DNA powder is charged to the sample-pouring port 52 of each of the micropipettes 34 via the introducing hole 104 of the fixing jig 36 from each of the tubes 106 respectively. Subsequently, the buffer solution is poured from the sample-pouring port 52 into the cavity 56 to prepare the sample solution. After that, a voltage of such a degree as to excite the vibration may be applied to the actuator section 58 to agitate and mix the liquid charged in the cavity 56 to prepare the sample solution. After completion of the preparation of the sample solution in the cavity 56, the actuator section 58 is driven to discharge and supply the sample solution onto the base plate 10.

Figure 7:
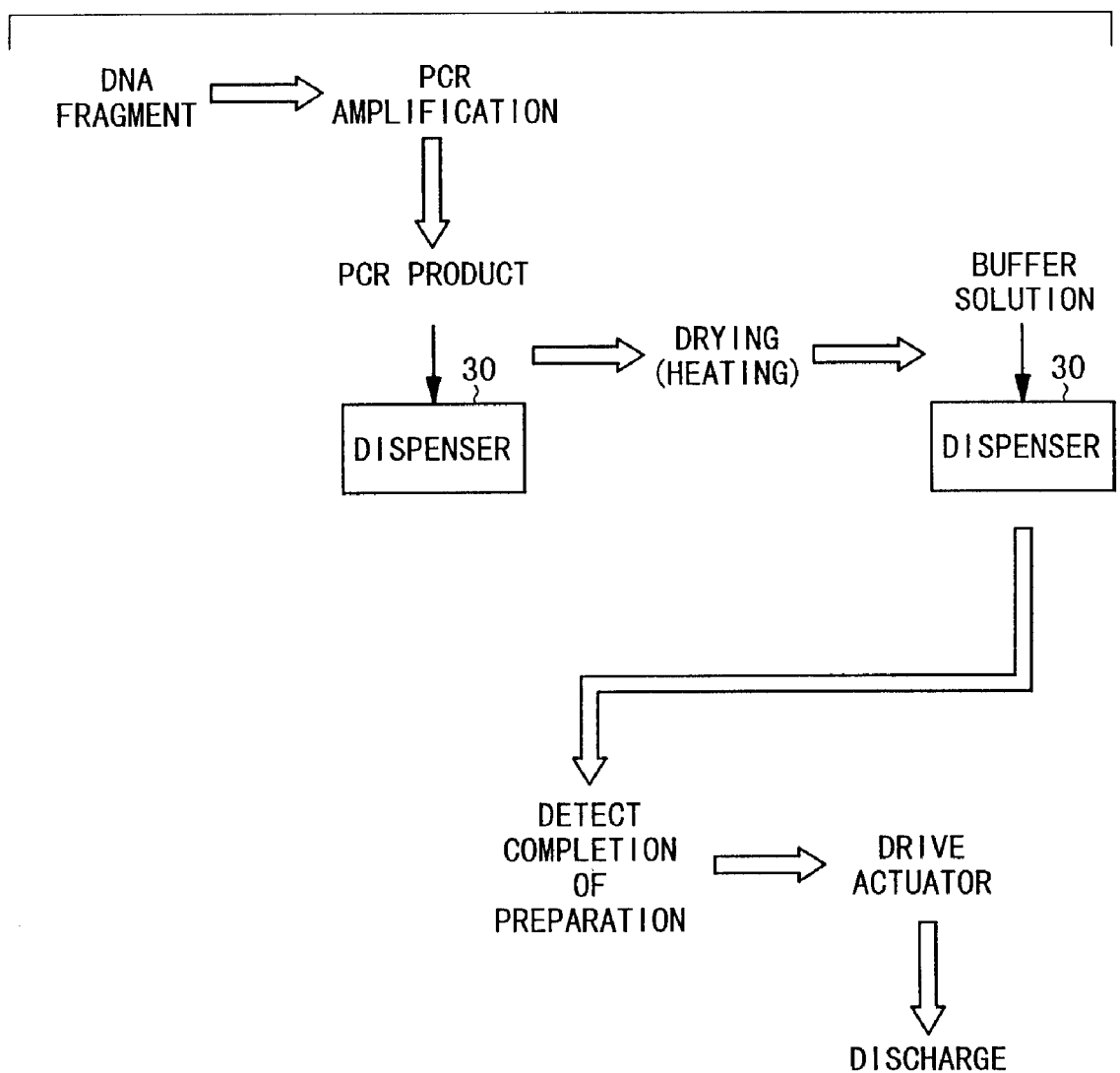
FIG. 7 illustrates a production method according to a second embodiment.

Next, a production method according to a second embodiment is shown in FIG. 7. At first, a DNA fragment is PCR-amplified to prepare a PCR product. After that, the PCR product is allowed to pass through the introducing hole 104 of the fixing jig 36 from each of the tubes 106 respectively, and it is charged into the cavity 56 from the sample-pouring port of each of the micropipettes 34.

After that, the substrate 50 is heated at a temperature of such a degree that DNA is not denatured. The PCR product is dried to prepare DNA powder. After that, a buffer solution is poured from the sample-pouring port 52 into the cavity 56 to prepare the sample solution. After that, a voltage of such a degree as to excite the vibration may be applied to the actuator section 58 to agitate and mix the liquid charged in the cavity 56 to prepare the sample solution. After completion of the preparation of the sample solution in the cavity 56, the actuator section 58 is driven to discharge and supply the sample solution onto the base plate 10.

Figure 8:
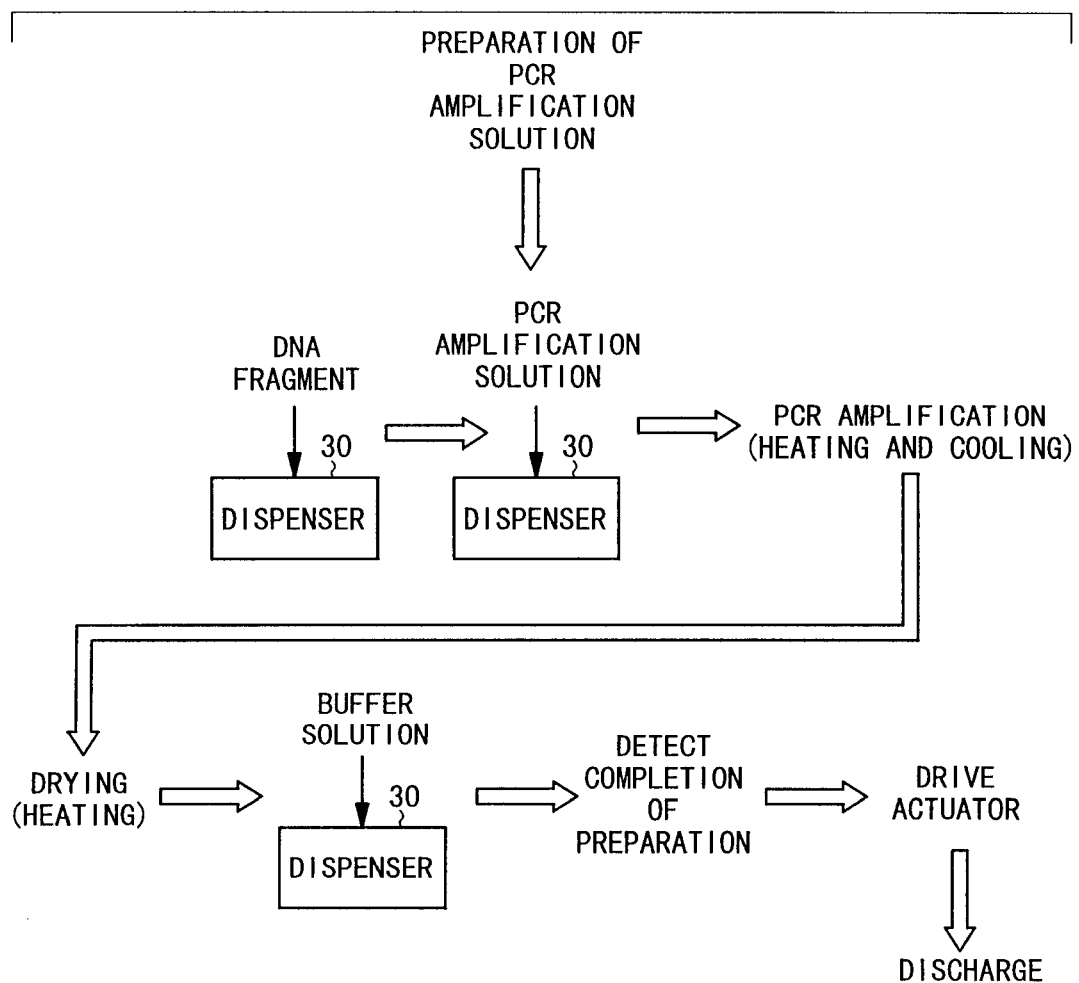
FIG. 8 illustrates a production method according to a third embodiment.

Next, a production method according to a third embodiment is shown in FIG. 8. At first, a DNA fragment is charged to the sample-pouring port 52 of each of the micropipettes 34 via the introducing hole 104 of the fixing jig 36 from each of the tubes 106 respectively. Subsequently, PCR amplification reagents (for example, primers, enzyme, PCR buffer solution, dNTP's, and distilled water) are poured from the sample-pouring port 52 into the cavity 56. After that, the substrate 50 is repeatedly heated and cooled to perform the PCR amplification in the cavity 56.

After that, the substrate 50 is heated at a temperature of such a degree that DNA is not denatured. The PCR product is dried to prepare DNA powder. After that, a buffer solution is poured from the sample-pouring port 52 into the cavity 56 to prepare the sample solution. After that, a voltage of such a degree as to excite the vibration may be applied to the actuator section 58 to agitate and mix the liquid charged in the cavity 56 to prepare the sample solution. After completion of the preparation of the sample solution in the cavity 56, the actuator section 58 is driven to discharge and supply the sample solution onto the base plate 10.

Figure 9:
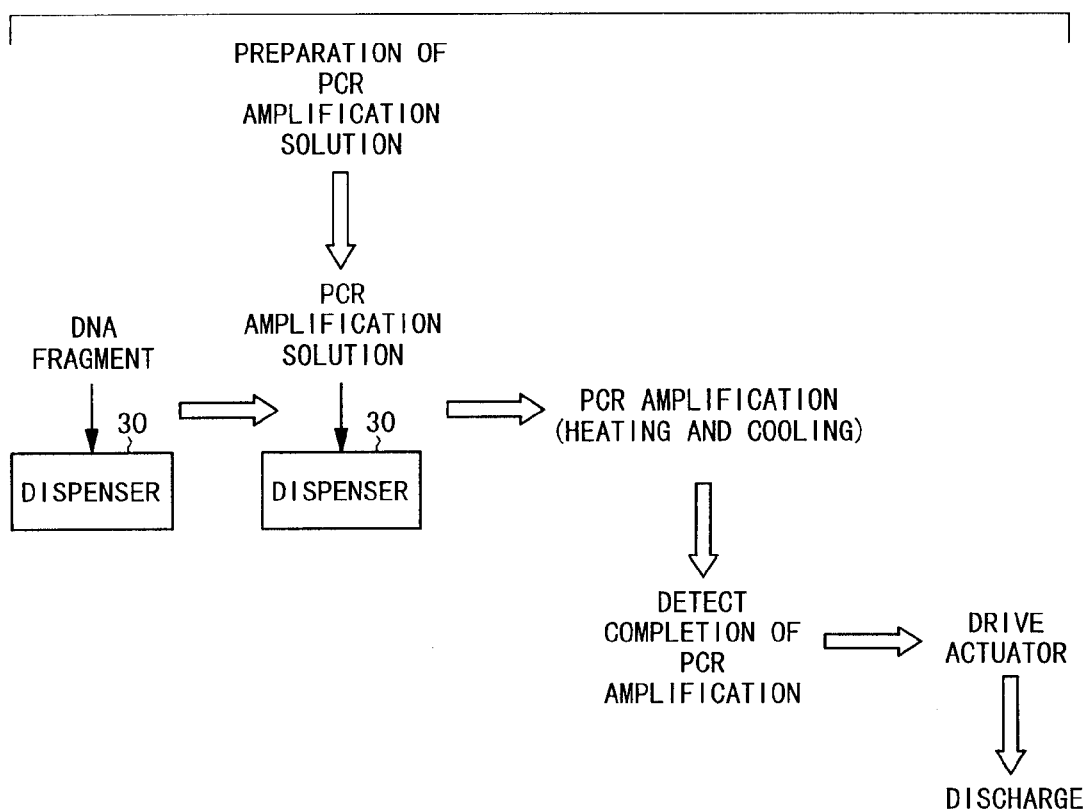
FIG. 9 illustrates a production method according to a fourth embodiment.

Next, a production method according to a fourth embodiment is shown in FIG. 9. At first, a DNA fragment is charged to the sample-pouring port 52 of each of the micropipettes 34 via the introducing hole 104 of the fixing jig 36 from each of the tubes 106 respectively. Subsequently, PCR amplification reagents (for example, primers, enzyme, PCR buffer solution, dNTP's, and distilled water) are poured from the sample-pouring port 52 into the cavity 56. After that, the substrate 50 is repeatedly heated and cooled to perform the PCR amplification in the cavity 56. After that, the actuator section 58 is driven to discharge and supply the sample solution onto the base plate 10.

The following methods are available to heat the interior of the cavity 56. That is, the interior of the cavity 56 may be heated together with the fixation plate 32 by using, for example, a heater. Alternatively, the substrate 50 may be heated by using, for example, laser beam, infrared ray, and electromagnetic wave. The following methods are available to cool the interior of the cavity 56. That is, the interior of the cavity 56 may be cooled by allowing an air-cooling type or water-cooling type cooling plate to contact with the fixation plate 32. Alternatively, a cooling agent composed of, for example, alternative freon gas or liquid nitrogen may be sprayed onto the substrate 50.

In the production method according to the third embodiment shown in FIG. 8, for example, isopropanol precipitation may be performed to concentrate objective DNA after the PCR amplification in the cavity 56, in order to reduce the impurity concentration of the PCR product and improve the quality of the DNA chip.

The following method is preferably adopted for isopropanol precipitation. That is, at first, isopropyl alcohol is poured into the cavity 56 from the sample-pouring port 52. After that, a voltage of such a degree as to excite the vibration is applied to the actuator section 58 to agitate and mix the liquid charged in the cavity 58. After that, the system is left to stand for about 20 minutes. After that, the respective tubes 106 and the through-holes 40 are sealed with a tape or the like. The whole dispenser system 30 is applied to a centrifugal machine to precipitate objective DNA. After that, the solution is removed from the tube 106 by using a pipette or the like. Thus, objective DNA is preferably concentrated.

It is preferable that the completion of the PCR amplification in the cavity 56 and the completion of the preparation of the sample solution are recognized by sensing the change of the fluid characteristic in the cavity 56.

In the present invention, the change of the fluid characteristic in the cavity 56 is recognized by applying a voltage in such a degree as to excite the vibration in the actuator section 58, and detecting the change of the electric constant caused by the vibration. Such a procedure for sensing the change of the fluid characteristic is disclosed, for example, in Japanese Laid-Open Patent Publication No. 8-201265.

Specifically, the electric connection from a power source for driving the discharge is separated from the actuator section 58 at a predetermined interval by using a relay. Simultaneously, a means for measuring the resonance frequency is connected by using the relay. At this point of time, the impedance or the resonance frequency is electrically measured.

Accordingly, it is possible to recognize, for example, whether or not the viscosity and the specific gravity of the liquid are those of the objective sample (liquid containing the DNA fragment or the like). That is, as for each of the micropipettes 34, the micropipette 34 itself functions as a sensor. Therefore, it is also possible to simplify the structure of the micropipette 34.

The actuator section 58 is driven under a driving condition corresponding to the amount of liquid droplets suitable for the required spot diameter, and the sample solution is repeatedly supplied. Accordingly, the DNA chip 20 is produced. Usually, when one minute spot 80 is formed, one to several hundred droplets are discharged from the micropipette 34.

When the amount of the sample in the sample-pouring port 52 is decreased, the discharge is continued by adding a buffer solution, purified water, or an aqueous solution containing sodium chloride so that no bubbles enter the inside of the flow passage. Accordingly, all of the sample can be used without allowing the sample solution to remain in the micropipette 34. The completion of the substitution from the sample to the substitution solution (completion of the sample discharge) is confirmed by detecting the viscosity and the specific gravity of the liquid by using the actuator section 58 in the same manner as described above.

The substitution between the substitution solution and the sample solution in the cavity 56 is performed in a form of laminar flow. However, when the type of sample solution is changed or when the movement speed of the liquid is extremely fast, it is not necessarily indispensable to use laminar flow at portions of the cavity 56 in the vicinity of the first communication hole 62. In this case, the purge amount of the sample solution is increased due to the mixing of the sample and the substitution solution. However, it is possible to suppress the increase in the purge amount to be minimum by judging the completion of the substitution by sensing the change of the fluid characteristic in the cavity 56.

It is preferable to use the substitution solution and the sample solution such that the existing gas in the solution is previously removed by performing a degassing operation. When such a solution is used, if any bubbles obstruct the flow passage at an intermediate portion to cause the defective charge upon the charge of the solution into the flow passage of the micropipette 34, then the inconvenience can be avoided by dissolving the bubble in the solution. Further, no bubbles are generated in the fluid during the discharge, and no defective discharge is caused.

As described above, in the method for producing the DNA chip according to the embodiment of the present invention, the process for mixing the DNA powder and the buffer solution to prepare the sample solution, the process for drying the PCR product to prepare the DNA powder followed by being mixed with the buffer solution to prepare the sample solution, or the process ranging from the PCR amplification to the preparation of the sample solution is performed in the identical dispenser 30.

Therefore, it is possible to perform the steps ranging from the preparation of the sample solution to the supply process or the steps ranging from the PCR amplification to the supply process can be performed in accordance with the series of steps without deteriorating the quality of the sample solution. Further, it is possible to realize the simplification of the preservation equipment for the sample solution. It is possible to reduce the cost and improve the quality of the DNA chip. It is unnecessary to perform any steps of transferring the sample solution to another vessel. Therefore, it is possible to improve the efficiency of utilization of the sample solution. Further, the steps ranging from the preparation of the sample solution to the supply process or the steps ranging from the PCR amplification to the supply process are performed in one dispenser 30. Therefore, the sample solution scarcely contacts with the atmospheric air. Thus, it is possible to avoid the deterioration of the quality of the sample solution.

It is a matter of course that the method for producing the DNA chip according to the present invention is not limited to the embodiments described above, which may be embodied in other various forms without deviating from the gist or essential characteristics of the present invention.

What is claimed is:

1. A method for producing a DNA chip by supplying a large number of sample solutions onto a base plate, comprising the steps of:

PCR-amplifying a DNA fragment to prepare a PCR product;

drying said PCR product to prepare DNA powder;

supplying said DNA powder into a solution supply apparatus; and supplying a buffer solution into said supply apparatus to prepare a sample solution, wherein:

said sample solution in said supply apparatus is supplied onto said base plate directly from said supply apparatus to produce said DNA chip.

2. The method for producing said DNA chip according to claim 1, wherein said sample solution is supplied in accordance with an ink-jet system.

3. The method for producing said DNA chip according to claim 1, wherein said supply apparatus is a dispenser comprising a plurality of arranged micropipettes each including a pouring port for pouring said sample solution from the outside, a cavity for pouring and charging said sample solution thereinto, and a discharge port for discharging said sample solution, formed on at least one or more substrates, said micropipette further including a piezoelectric/electrostrictive element disposed on at least one wall surface of said substrate which forms said cavity so that said sample solution is movable in said cavity, and mutually different types of said sample solutions being discharged from said discharge ports of said respective micropipettes.

4. The method for producing said DNA chip according to claim 3, wherein the completion of the preparation of said sample solution in each of said plurality of cavities is recognized by sensing a change of a fluid characteristic in said cavity.

5. A method for producing a DNA chip by supplying a large number of sample solutions onto a base plate, comprising the steps of:

PCR-amplifying a DNA fragment to prepare a PCR product;

supplying said prepared PCR product into a solution supply apparatus;

drying said PCR product in said supply apparatus to prepare DNA powder; and supplying a buffer solution into said supply apparatus to prepare a sample solution, wherein:

said sample solution in said supply apparatus is supplied onto said base plate by using said supply apparatus to produce said DNA chip.

6. The method for producing said DNA chip according to claim 5, wherein said sample solution is supplied in accordance with an ink-jet system.

7. The method for producing said DNA chip according to claim 5, wherein said supply apparatus is a dispenser comprising a plurality of arranged micropipettes each including a pouring port for pouring said sample solution from the outside, a cavity for pouring and charging said sample solution thereinto, and a discharge port for discharging said sample solution, formed on at least one or more substrates, said micropipette further including a piezoelectric/electrostrictive element disposed on at least one wall surface of said substrate which forms said cavity so that said sample solution is movable in said cavity, and mutually different types of said sample solutions being discharged from said discharge ports of said respective micropipettes.

8. The method for producing said DNA chip according to claim 7, wherein the completion of the preparation of said sample solution in each of said plurality of cavities is recognized by sensing a change of a fluid characteristic in said cavity.

9. A method for producing a DNA chip by supplying a large number of sample solutions onto a base plate, comprising the steps of:

PCR-amplifying a DNA fragment to prepare a PCR product in a solution supply apparatus;

drying said PCR product in said supply apparatus to prepare DNA powder; and supplying a buffer solution into said supply apparatus to prepare a sample solution, wherein:

said sample solution in said supply apparatus is supplied onto said base plate by using said supply apparatus to produce said DNA chip.

10. The method for producing said DNA chip according to claim 9, wherein said sample solution is supplied in accordance with an ink-jet system.

11. The method for producing said DNA chip according to claim 9, wherein said supply apparatus is a dispenser comprising a plurality of arranged micropipettes each including a pouring port for pouring said sample solution from the outside, a cavity for pouring and charging said sample solution thereinto, and a discharge port for discharging said sample solution, formed on at least one or more substrates, said micropipette further including a piezoelectric/electrostrictive element disposed on at least one wall surface of said substrate which forms said cavity so that said sample solution is movable in said cavity, and mutually different types of said sample solutions being discharged from said discharge ports of said respective micropipettes.

12. The method for producing said DNA chip according to claim 11, wherein the completion of the preparation of said sample solution in each of said plurality of cavities is recognized by sensing a change of a fluid characteristic in said cavity.

13. A method for producing a DNA chip by supplying a large number of sample solutions onto a base plate, comprising the step of:

PCR-amplifying a DNA fragment to prepare a PCR product in a solution supply apparatus, wherein:

said sample solution after preparation in said supply apparatus is supplied onto said base plate by using said supply apparatus to produce said DNA chip.

14. The method for producing said DNA chip according to claim 13, wherein said sample solution is supplied in accordance with an ink-jet system.

15. The method for producing said DNA chip according to claim 13, wherein said supply apparatus is a dispenser comprising a plurality of arranged micropipettes each including a pouring port for pouring said sample solution from the outside, a cavity for pouring and charging said sample solution thereinto, and a discharge port for discharging said sample solution, formed on at least one or more substrates, said micropipette further including a piezoelectric/electrostrictive element disposed on at least one wall surface of said substrate which forms said cavity so that said sample solution is movable in said cavity, and mutually different types of said sample solutions being discharged from said discharge ports of said respective micropipettes.

16. The method for producing said DNA chip according to claim 15, wherein the completion of the preparation of said sample solution in each of said plurality of cavities is recognized by sensing a change of a fluid characteristic in said cavity.

* * * * *